United States Patent [19]

Fogal et al.

[11] Patent Number: 5,758,942
[45] Date of Patent: Jun. 2, 1998

[54] MECHANICAL VISION SYSTEM USING SELECTIVE WAVELENGTH AND BRIGHTNESS ILLUMINATION

[75] Inventors: Rich Fogal; Michael B. Ball; Mike Bettinger. all of Boise, Id.

[73] Assignee: Micron Technology, Inc., Boise, Id.

[21] Appl. No.: 574,108

[22] Filed: Dec. 18, 1995

[51] Int. Cl.⁶ ................................................ G03B 15/02
[52] U.S. Cl. .................... 362/12; 362/11; 362/231; 362/295; 362/800
[58] Field of Search ............................ 362/231, 234, 362/11, 12, 295, 800; 348/131

[56] References Cited

U.S. PATENT DOCUMENTS

| | | | |
|---|---|---|---|
| 4,677,473 | 6/1987 | Okamoto et al. | 348/126 |
| 5,119,435 | 6/1992 | Berkin | 382/8 |
| 5,367,439 | 11/1994 | Mayer et al. | 362/32 |
| 5,384,519 | 1/1995 | Gotoh | 315/324 |
| 5,457,492 | 10/1995 | Sasaki et al. | 348/131 X |

Primary Examiner—Stephen F. Husar
Attorney, Agent, or Firm—Craig M. Korfanta

[57] ABSTRACT

An illumination subsystem which is used in conjunction with a mechanical vision system and which has a plurality of intensity adjustable monochromatic light sources, at least two of which are of different wavelength illumination. An oblique illumination assembly is positioned off to the side of the video camera and is pointed at the subject to be viewed. A direct illumination assembly is positioned within the light path of the lens of the camera to facilitate direct illumination of the subject. The intensity of the emitters as well as there colors can be adjusted to provided optimum recognition for the mechanical vision system.

7 Claims, 3 Drawing Sheets

MECHANICAL VISION SYSTEM USING SELECTIVE WAVELENGTH AND BRIGHTNESS ILLUMINATION

BACKGROUND OF THE INVENTION

1. Technical Field

This invention generally relates to mechanical visions systems and more particularly, this invention relates to using selective wavelengths and brightness' of illumination to optimize pattern recognition of components such as chips and semiconductor dies.

2. Background

Mechanical vision systems are used in semiconductor manufacture to aid in placement of dies on leadframes, wire bonding of the dies to the leadframe, placement and bonding of chips on multichip module substrates, inspection and quality control. These systems employ a video camera to produce a highly magnified image of a component which can be viewed by an operator or analyzed by a pattern recognition algorithm to aid in the positioning of tooling such as a wire bonding head.

U.S. Pat. Nos. 4,441,205, 4,853,968 and 5,119,435 teach one such system. This particular system creates a digital image of the subject by assembling an array of pixels which are each obtained by converting an analog signal to a four bit word whose value corresponds to the magnitude of the intensity of the reflection of light received from a portion of the subject.

The light sources which are known to the inventors for illuminating the subjects are monochromatic and consist of one or more red light emitting diodes (LEDs). Some surface features tend to obscure using a single monochromatic light source. Additionally, because different surfaces reflect light differently because of their texture and color some components simply do not show up well under monochromatic illumination. Increasing the intensity of monochromatic illumination can bring out the obscured features however this can cause prominent features to wash out as the light sensors in the video camera become saturated.

What is needed is tunable illumination source which uses limited multiple wavelength sources which each can be adjusted to provide an optimum combination of colors and intensities of illumination for a mechanical vision system.

SUMMARY OF THE INVENTION

This object and others is accomplished by an illumination subsystem which is used in conjunction with a mechanical vision system and which has a plurality of intensity adjustable monochromatic light sources, at least two of which are of different wavelength illumination.

The invention provides for both oblique and normal incidence of multiple wavelength illumination. An oblique illumination assembly is positioned off to the side of the video camera and is pointed at the subject to be viewed. A direct illumination assembly is positioned within the light path of the lens of the camera to facilitate direct illumination of the subject. At least one of the illumination assemblies, preferably both, contains at least two different wavelength light emitters, such as two differently colored LEDs. Each of the emitters is preferably separately controllable to adjust its intensity. However, the emitters may be controllable by one or more group controls, where for instance the emitters may be grouped by color, so that the intensity of all the members of a group can be adjusted at the same time.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentality's and combinations particularly pointed out in the appended claims.

DESCRIPTION OF THE PREFERRED EMBODIMENT

Figure 1:
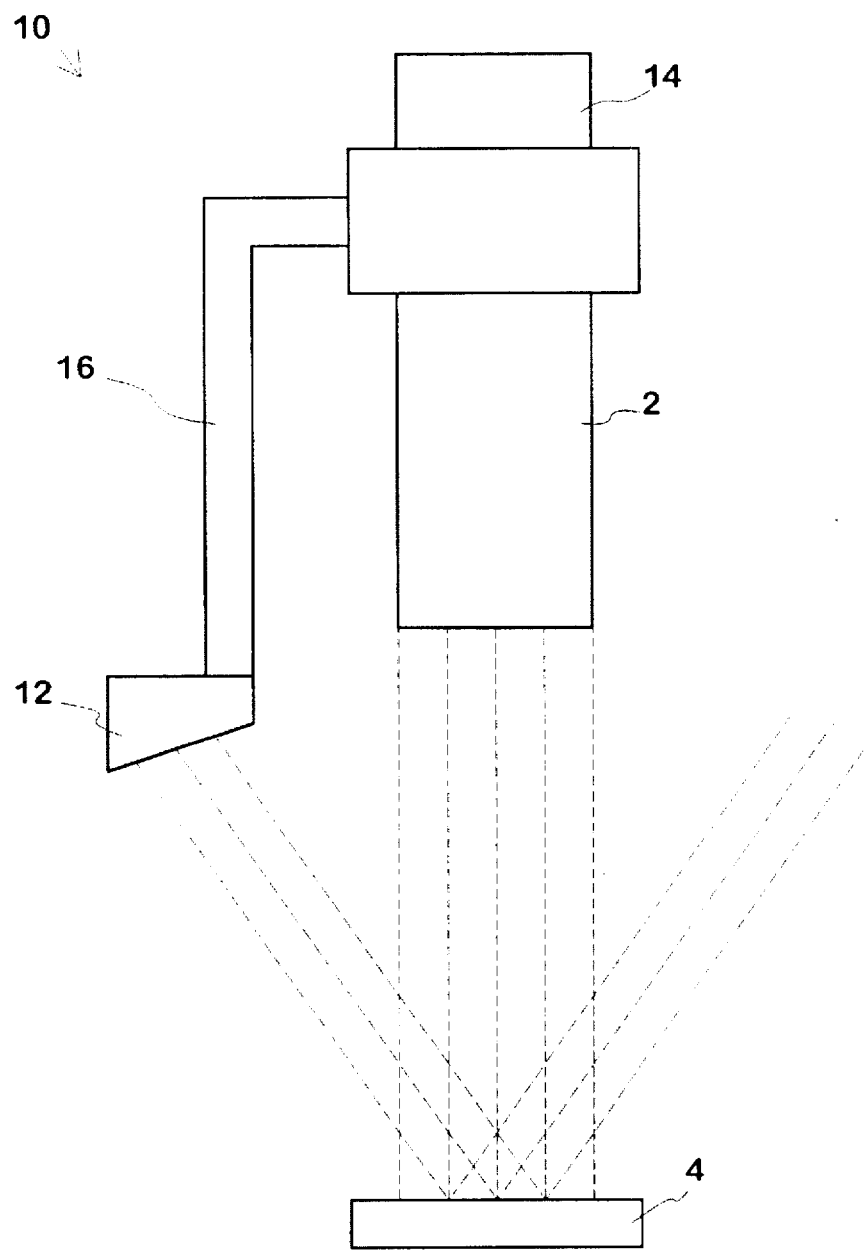
FIG. 1 is a schematic representation of a mechanical vision system using a multiple wavelength illumination assembly according to the invention.
Figure 3:
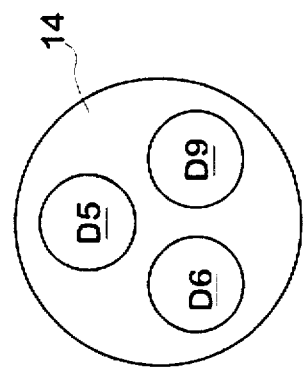
FIG. 3 is a bottom plan view of the direct illumination subassembly.
Figure 2:
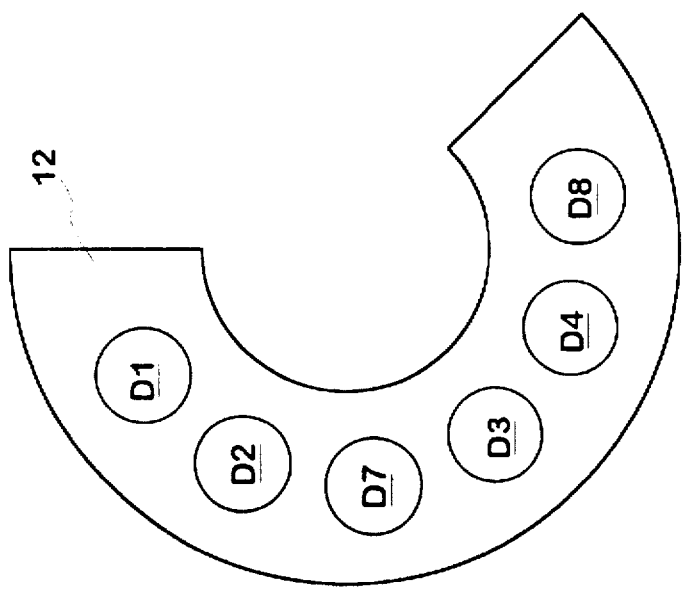
FIG. 2 is a bottom plan view of the oblique illumination subassembly.

Referring now to the figures, a multiple monochromatic wavelength illumination assembly is generally designated as 10 and is shown attached to a video camera 2 typical of those used in mechanical vision systems. The illumination is monochromatic multiple wavelength in the sense that it comprises two or more separate narrow band wavelengths of light.

In this preferred embodiment, multiple monochromatic wavelength assembly 10, hereinafter simply illumination assembly 10, has an oblique illumination subassembly 12 attached adjacent to the aperture of camera 2 by a bracket 16 which is attached to the main body of camera 2 and a direct illumination subassembly 14 fixed in the light path of camera 2.

Oblique illumination subassembly 12 here has a semicircular body to which a plurality of light emitters are attached. In this embodiment, the light emitters are two different colored LEDs, yellow LEDs D1–D4 and orange LEDs D7 and D8. Subassembly 12 is positioned the direct light toward subject 4 such that the general angle of reflection is away from the light path of camera 2. In this sense, subassembly 12 provides a diffused light source for camera 2.

Direct illumination subassembly 14 is attached to camera 2 and positioned to emit multiple monochromatic wavelengths of light into the light path of camera 2. This illumination provides the normally incident illumination for subject 4. The light which is reflected into the lens of camera 2 to render the video image is a combination of light emitted from subassembly 12 and subassembly 14. The inventors have found that the combination of yellow and orange light in a 2:1 ratio provides excellent resolution for a wide range of semiconductor manufacturing applications. However, depending upon the geometry, colors and surface qualities of the subject components other color combinations might be more beneficial.

Figure 4:
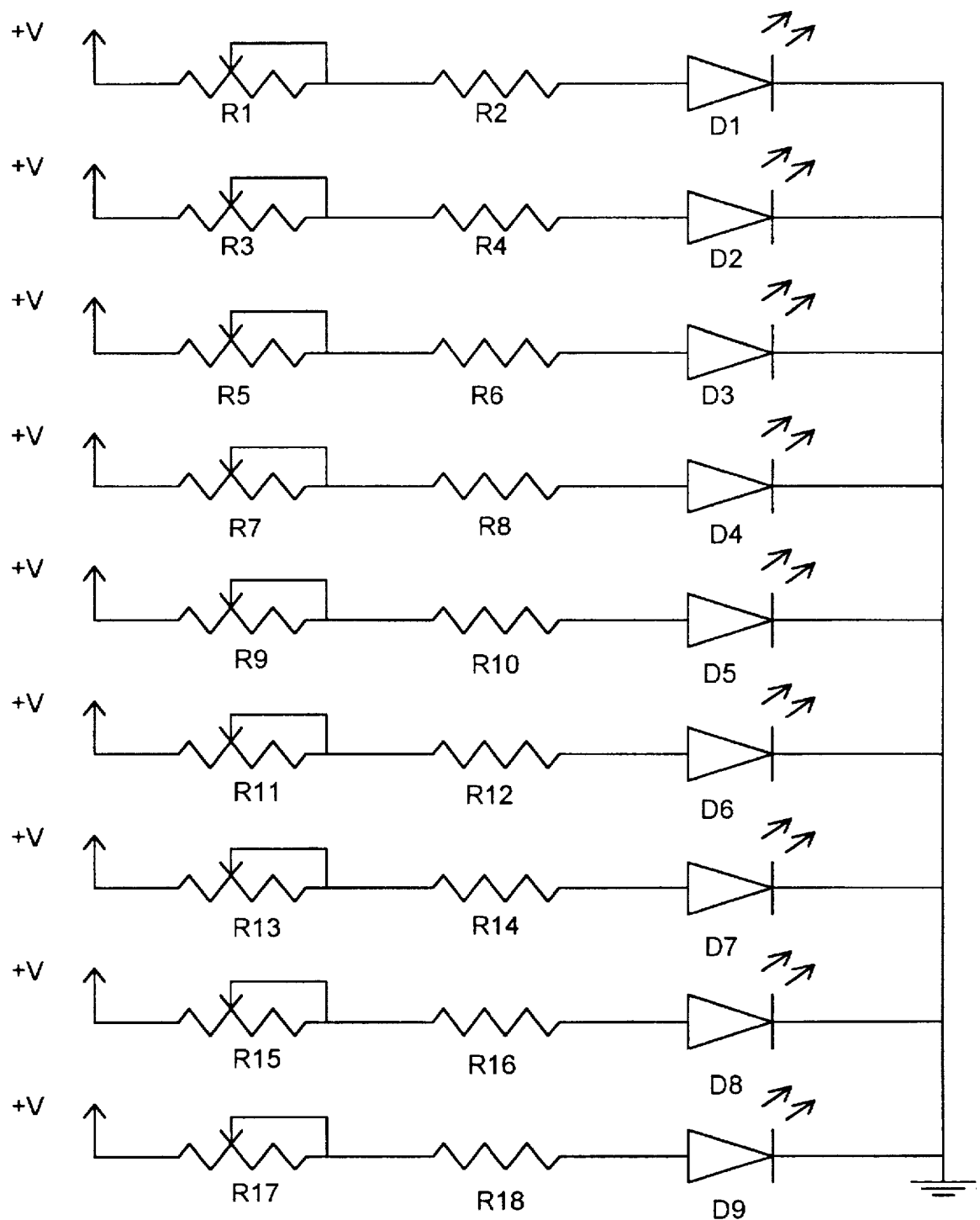
FIG. 4 is a simplified circuit schematic of an LED driver for an LED illumination source.

The LEDs are driven by one or more emitter source driver circuits. One such circuit is illustrated in FIG. 4. Here, each LED D1–D9 is driven by a series resistor network having a current limiting resistor R2, R4, . . . R18 and a variable resistor R1, R3 . . . R17 for brightness control. This particular configuration provides only individual control of each LED. However, it may be desirable to control the LEDs as a single group or as multiple groups. For instance, grouping yellow LEDs D1–D6 as one group and orange LEDs D7–D9 as a second group. A single actuator, either mechanical or electrical, can be used to control the variable resistors of all the members of the group at once. Alternatively, a second set of variable resistors under single group control could be added to enable both individual and group control.

In use, the operator adjusts the intensity of the various emitters as well as their wavelengths, i.e. colors, to optimize the visual image captured by camera 2. This is accomplished empirically by the operator viewing a video monitor, not shown in the figures, which is connected to camera 2 for viewing the image it produces. It can also be determined analytically by bracketing a series of exposures using different combinations of intensities and wavelengths and quantifying the recognition accuracy for each configuration.

While there is shown and described the preferred embodiment of the invention, it is to be distinctly understood that this invention is not limited thereto but may be variously embodied to practice within the scope of the following claims.

We claim:

1. An illumination source for a mechanical vision system comprising:

a first monochromatic light emitting source of known wavelength;

a second monochromatic light emitting source having a wavelength different from that of the first light emitting source;

a first illumination subassembly carrying light emitting sources each positioned with respect to the mechanical vision system to provide diffuse illumination of an object to be viewed; and a second illumination subassembly carrying light emitting sources each positioned with respect to the mechanical vision system to provide direct illumination of an object to be viewed, where the light sources on both subassemblies are selected from the first and second monochromatic light emitting sources.

2. The illumination source of claim 1 further comprising a brightness control circuit electrically connected to the first and second light sources for controlling their brightness.

3. A mechanical vision system comprising:

a video camera;

a first monochromatic light emitting source of known wavelength positioned with respect to the video camera to illuminate an object to be viewed by the camera; and a second monochromatic light emitting source having a wavelength different from that of the first light emitting source also positioned to illuminate the object to be viewed.

4. The vision system of claim 3 further comprising a brightness control circuit electrically connected to the first and second light sources for controlling their brightness.

5. The vision system of claim 4 further comprising:

a first illumination subassembly carrying light emitting sources each positioned with respect to the video camera to provide diffuse illumination of an object to be viewed; and a second illumination subassembly carrying light emitting sources each positioned with respect to the video camera to provide direct illumination of an object to be viewed, where the light sources on both subassemblies are selected from the first and second monochromatic light emitting sources.

6. The vision system of claim 3 further comprising:

a first illumination subassembly carrying light emitting sources each positioned with respect to the video camera to provide diffuse illumination of an object to be viewed; and a second illumination subassembly carrying light emitting sources each positioned with respect to the video camera to provide direct illumination of an object to be viewed, where the light sources on both subassemblies are selected from the first and second monochromatic light emitting sources.

7. The vision system of claim 5 wherein the first monochromatic light sources are yellow LEDs and the second monochromatic light sources are orange LEDs.

* * * * *